United States Patent
Thorwart et al.

[11] Patent Number: 5,922,868
[45] Date of Patent: Jul. 13, 1999

[54] USE OF XANTHINE DERIVATIVES FOR THE TREATMENT OF NERVE DAMAGE FOLLOWING AN INTERRUPTION IN BLOOD CIRCULATION

[75] Inventors: Werner Thorwart, Hochheim am Main; Harald Furrer; Erhard Wolf, both of Hofheim/Ts; Ulrich Gebert, Glashütten/Ts; Erhard Rossmanith, Schwalbach/Taunus; John J. Grome, Wiesbaden; Ernst-Jürgen Schneider, Bad Camberg, all of Germany

[73] Assignee: Hoechst Aktiengesellschaft, Frankfurt am Main, Germany

[21] Appl. No.: 08/576,936

[22] Filed: Dec. 22, 1995

Related U.S. Application Data

[63] Continuation of application No. 08/418,962, Apr. 7, 1995, abandoned, which is a continuation of application No. 08/063,803, May 20, 1993, abandoned.

[30] Foreign Application Priority Data

May 20, 1992 [DE] Germany .............................. 42 16 711

[51] Int. Cl.⁶ .................. A61K 31/52; C07D 473/04; C07D 473/08
[52] U.S. Cl. .............................. 544/267; 544/271
[58] Field of Search .................... 544/271, 273, 544/267; 514/263

[56] References Cited

U.S. PATENT DOCUMENTS

| | | | |
|---|---|---|---|
| 3,737,433 | 6/1973 | Mohler | 544/271 |
| 4,242,345 | 12/1980 | Brenner | 544/271 |
| 4,289,776 | 9/1981 | Mohler | 544/271 |
| 4,372,959 | 2/1983 | Goring | 544/271 |
| 4,833,146 | 5/1989 | Gebert | 544/267 |
| 4,845,102 | 7/1989 | Sakuri | 544/271 |
| 5,082,845 | 1/1992 | Wolf | 544/271 |
| 5,109,003 | 4/1992 | Tanaka | 544/267 |
| 5,310,666 | 5/1994 | Aretz | 435/119 |

FOREIGN PATENT DOCUMENTS

| | | | |
|---|---|---|---|
| 260127 | 3/1988 | European Pat. Off. | 544/271 |
| 269841 | 6/1988 | European Pat. Off. | 544/271 |

OTHER PUBLICATIONS

Miyamoto, J Med Chem 36(10) 1380 (May 14, 1993).
Klosa, Chem Abs 51, 1195e,f (1956.
Ruffini, Chem Abs 51, 8975 f (1955.
Brierly in "Greenfields Neuropathology," 4th Ed, pp. 125–156 (1984).
Goodman, Ed, "Pharmacological Basts of Therapeutics," 5th Ed (1975) pp. 882–893.
Hayashi, Chem Pharm Bull 16(3), 426(1968).
Romieh, Egypt. J. Pharm. Sci 34, 455(1993).

*Primary Examiner*—Mark L. Berch
*Attorney, Agent, or Firm*—Finnegan, Henderson, Farabow, Garrett & Dunner, L.L.P.

[57] ABSTRACT

Use of xanthine derivatives for the treatment of nerve damage following an interruption in blood circulation.

The invention relates to the use of xanthine derivatives of the formula I

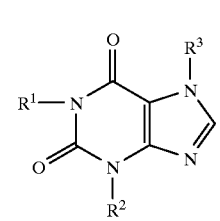

(I)

in which $R^2$ is a $(C_1-C_4)$-alkyl group and at least one of the symbols $R^1$ and $R^3$ is a radical of the formula II or III

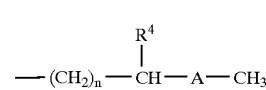

(II)

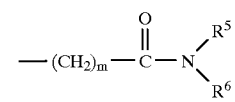

(III)

in which A is CHOH, CO or dioxolane, $R^4$ is a hydrogen atom or a $(C_1-C_4)$-alkyl group and n is 0 to 5, and in which $R^5$ and $R^6$ are hydrogen atoms or $(C_1-C_4)$-alkyl groups or, together with the nitrogen atom to which they are bonded, form a 5- to 7-membered ring, it being possible for one carbon atom to be replaced by an oxygen or nitrogen atom, m is 1 or 2 and the other radical $R^1$ or $R^3$, if appropriate, is a hydrogen atom, a $(C_1-C_6)$-alkyl group or a $(C_3-C_6)$-alkenyl group, for the preparation of medicaments for the prophylaxis and treatment of nerve damage following an interruption in blood circulation, and novel xanthine derivatives, and to processes for their preparation.

5 Claims, No Drawings

USE OF XANTHINE DERIVATIVES FOR THE TREATMENT OF NERVE DAMAGE FOLLOWING AN INTERRUPTION IN BLOOD CIRCULATION

This is a continuation of application Ser. No. 08/418,962 filed Apr. 7, 1995, now abandoned, which is a continuation of application Ser. No. 08/063,803 filed May 20, 1993, now abandoned.

A number of oxoalkyl- and hydroxyalkylxanthines stimulate blood flow and can also be used for disturbances in cerebral blood flow (U.S. Pat. No. 4,289,776, PCT 86/00401, U.S. Pat. No. 3,737,433). Processes for the preparation of the above-mentioned xanthine derivatives are also known (U.S. Pat. No. 4,289,776; U.S. Pat. No. 3,737,433).

No medicaments which allow the period of symptom-free interruption in blood circulation to be prolonged or which lead to a significant reduction in the nerve damage caused by the interruption in blood circulation are known to date. A first consequence of interruption in blood circulation is the deficient supply of oxygen to the areas affected, leading to metabolic disturbances.

It has now been found that the xanthine derivatives according to the invention are suitable for prolonging the period of symptom-free interruption in blood circulation, reducing the nerve damage which occurs following an interruption in blood circulation and increasing the partial pressure of oxygen in the brain.

The invention therefore relates to the use of at least one xanthine derivative of the formula I

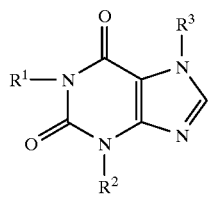

(I)

in which $R^2$ is an alkyl group having 1 to 4 carbon atoms and a) at least one of the radicals $R^1$ and $R^3$ is a straight-chain or branched radical of the formula II

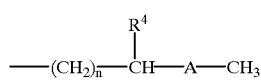

(II)

in which A is

1) —CH—,
   |
   OH

2) —C—  or
   ‖
   O

3) —C—
   / \
   O   O
   \_/

$R^4$ is 1) a hydrogen atom or 2) a $(C_1-C_4)$-alkyl group and n is an integer from 0 to 5, or b) at least one of the radicals $R^1$ and $R^3$ is a radical of the formula III

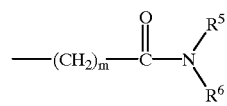

(III)

in which $R^5$ and $R^6$ are identical or different and independently of one another are a hydrogen atom or an alkyl group having 1 to 4 carbon atoms, or $R^5$ and $R^6$ together with the nitrogen atom to which they are bonded, form a 5- to 7-membered ring, which optionally contains a further hetero atom in the form of oxygen or nitrogen instead of one of the ring carbon atoms, it also being possible for the further nitrogen atom to be substituted by a $(C_1-C_4)$-alkyl group, m is the integer 1 or 2 and the other radical $R^1$ or $R^3$ which is present, if appropriate, is 1) a hydrogen atom, 2) a straight-chain or branched $(C_1-C_6)$-alkyl group, 3) a straight-chain or branched $(C_1-C_6)$-alkyl group, in which the carbon chain is interrupted by 1 or 2 oxygen atoms which are not bonded to one another, or 4) a straight-chain or branched $(C_3-C_6)$-alkenyl group, excluding 1-(5-oxohexyl) -3-methyl-7-n-propylxanthine, for the preparation of medicaments for the prophylaxis and treatment of nerve damage following an interruption in blood circulation.

The interruption in blood circulation can occur due to tourniquets or ligature clamps, for example in order to obtain a blood-free operating field, and due to arterial or venous occlusion or blockage caused by embolic or thrombotic obstructions in blood vessels. The blood circulation is interrupted, for example, during vascular surgery operations, such as removal of thrombi, during organ transplants, such as heart or kidney, and in cases of obstructions in arteries or veins, such as occur, for example, after a stroke, apoplexy or cardiac infarction. More or less severe nerve damage occurs, depending on the duration of the interruption in blood circulation, and may extend from mild disturbances in nerve performance to complete failure of the nerves, such as, for example, paralyses. Examples of symptoms of this nerve damage which may be mentioned are: disturbances in the membrane potential of the nerves, mental confusion of the patient, disorientation, absence of responsiveness by the patient, memory disturbances, lack of concentration, motor disturbances or paralyses. The blood circulation may be interrupted completely or partly, and as a result more or less severe nerve damage is to be observed.

Xanthine derivatives of the formula I in which $R^2$ is an alkyl group having 1 to 2 carbon atoms and at least one of the radicals $R^1$ and $R^3$ is a straight-chain or branched radical of the formula II, in which A is 1) 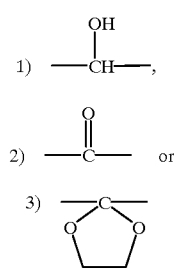

$R^4$ is a hydrogen atom or a $(C_1-C_2)$-alkyl group and
n is an integer from 2 to 5,
and the other radical $R^1$ or $R^3$ which is present, if appropriate, is
  1) a hydrogen atom,
  2) a straight-chain or branched $(C_1-C_6)$-alkyl group,
  3) a straight-chain or branched $(C_1-C_6)$-alkyl group, in which the carbon chain is interrupted by 1 or 2 oxygen atoms, or
  4) a straight-chain or branched $(C_3-C_6)$-alkenyl group,
excluding 1-(5-oxohexyl)-3-methyl-7-n-propylxanthine, are preferably employed.

5- to 7-membered rings are e.g. pyrrole, pyrroline, pyrolidine, pyridine, tetrahydropyridine, piperidine, azepine, pyrazole, imidazole, pyrazoline, imidazoline, pyrazolidine, imidazolidine, pyridazine, pyrimidine, pyrazine, piperazine, diazepine, oxazole, isoxazole, 2-isoxazoline, isoxazolidine or morpholine.

The invention furthermore relates to novel xanthine derivatives of the formula I in which $R^2$ is an alkyl group having 1 to 4 carbon atoms and
  a) at least one of the radicals $R^1$ and $R^3$ is a straight-chain or branched radical of the formula II, in which A is

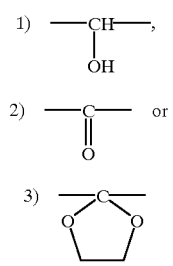

R is a $(C_1-C_4)$-alkyl group and
n is an integer from 2 to 5, or
  b) at least one of the radicals $R^1$ and $R^3$ is a radical of the formula III in which
$R^5$ and $R^6$ are identical or different and independently of one another are a hydrogen atom or a $(C_1-C_4)$-alkyl group, or $R^5$ and $R^6$, together with the nitrogen atom to which they are bonded, form a 5- to 7-membered ring, which optionally contains a further hetero atom in the form of oxygen or nitrogen instead of one of the ring carbon atoms, it also being possible for the further nitrogen atom to be substituted by a $(C_1-C_4)$-alkyl group,
m is the integer 1 or 2
and the other radical $R^1$ or $R^3$ which is present, if appropriate, is
  1) a hydrogen atom,
  2) a straight-chain or branched $(C_1-C_6)$-alkyl group,
  3) a straight-chain or branched $(C_1-C_4)$-alkyl group, in which the carbon chain is interrupted by 1 or 2 oxygen atoms, or
  4) a straight-chain or branched $(C_3-C_5)$-alkenyl group.

The invention furthermore relates to processes for the preparation of the novel xanthine derivatives, one embodiment comprising, for example,
  a) reacting xanthine derivatives of the formula I, in which $R^2$ is an alkyl group having 1 to 4 carbon atoms and $R^1$ and $R^3$ are hydrogen atoms, with an alkylating agent of the formula IV

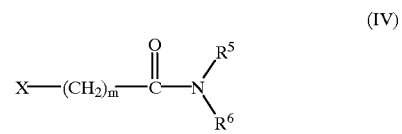

(IV)

or an alkylating agent of the formula $R^3$-X, in which X is halogen, such as chlorine, bromine or iodine, or is a sulfonic acid ester grouping and $R^3$, $R^4$, $R^5$, $R^6$, n and m have the abovementioned meanings, but $R^3$ is not a hydrogen atom, to give a disubstituted xanthine derivative of the formula V

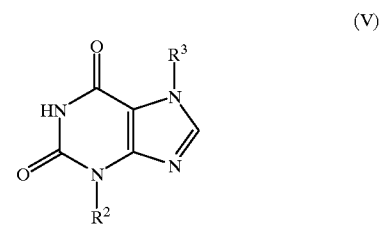

(V)

and if appropriate alkylating the xanthine derivative of the formula V in the position of $R^1$ with one of the abovementioned alkylating agents or an alkylating agent of the formula $R^1$-X in the presence of a basic agent or in the form of its salts, or
  b) reacting 1,3-disubstituted xanthine derivatives of the formula VI

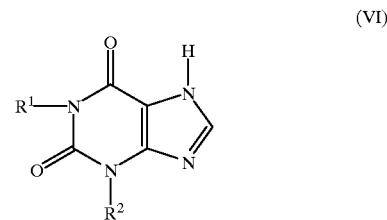

(VI)

in which $R^1$ and $R^2$ have the abovementioned meanings, with an alkylating agent of the formula IV or $R^3$-X in the presence of basic agents or in the form of their salts, or
  c) reducing xanthine derivatives of the formula I, in which $R^1$ or $R^3$ is an oxoalkyl radical, with customary reducing agents to give the corresponding hydroxy-alkylated xanthine derivatives.

The invention also relates to medicaments which comprise an active content of at least one xanthine derivative of the formula I, in addition to pharmaceutically suitable and physiologically tolerated excipients, additives and/or other active compounds and auxiliaries.

The medicaments according to the invention can be administered orally, topically, rectally, intravenously or, if appropriate, also parenterally. They can be administered before, after or during the interruption in blood circulation.

On the basis of the pharmacological properties of the xanthine derivatives according to the invention, these compounds can be used in all operations in hospitals or outpatient care where blood circulation to tissues, organs or extremities is completely or partly interrupted. These compounds furthermore can also be used during meniscus operations or diagnostic interventions where a complete or partial interruption of the blood circulation in the tissue affected occurs.

The xanthines according to the invention are particularly suitable for the prophylaxis and reduction of nerve damage which occurs following obstructions in the blood vessels of arterial or venous origin.

The interruption in blood circulation should last not much longer than 240 minutes, preferably 5 to 120 30 minutes, in particular 10 to 30 minutes. The duration of the largely complication-free interruption in blood circulation essentially depends on whether the interruption is partial or complete and what tissue or organs are cut off from the blood circulation. The expert can easily determine the time limits of the interruption.

The invention also relates to a process for the preparation of a medicament according to the invention, which comprises incorporating at least one xanthine derivative of the formula I into a suitable presentation form together with a pharmaceutically suitable and physiologically tolerated excipient and if appropriate other suitable active compounds, additives or auxiliaries.

Suitable solid or liquid pharmaceutical formulation forms are, for example, granules, powders, coated tablets, tablets, (micro)capsules, suppositories, syrups, elixirs, suspensions, emulsions, drops or injectable solutions, and also preparations with a protracted release of active compound, the customary auxiliaries, such as excipients, disintegrating agents, binders, coating agents, swelling agents, anti-friction agents or lubricants, flavoring substances, sweeteners and solubilizing agents, being used for their preparation. As auxiliaries which are often used there may be mentioned, for example, magnesium carbonate, titanium dioxide, lactose, mannitol and other sugars, talc, lactalbumin, gelatin, starch, cellulose and their derivatives, animal and vegetable oils, polyethylene glycols and solvents, such as, for example, sterile water and mono- or polyhydric alcohols, for example glycerol.

The pharmaceutical preparations are preferably prepared and administered in dosage units, each unit comprising, as the active constituent, a particular dose of the xanthine derivatives of the formula I according to the invention. In the case of solid dosage units, such as tablets, capsules, coated tablets or suppositories, this dose can be up to about 300 mg, but preferably about 10 to 100 mg.

For treatment of a patient (70 kg) who has to undergo vascular surgery treatment, a dose of the xanthine derivatives of the formula I according to the invention of 400 to 1200 mg per day and patient is indicated before, during and after the operation.

Under certain circumstances, however, higher or lower doses may also be appropriate. The dose can be administered either by a single administration in the form of an individual dosage unit or several smaller dosage units, or by multiple administrations of subdivided doses at certain intervals of time.

Finally, the xanthine derivatives of the formula I according to the invention can also be formulated, during preparation of the abovementioned pharmaceutical formulation forms, together with other suitable active compounds, for example active compounds which trap free oxygen radicals, for example 1,5-dihydro-4H-pyrazolo(3,4-d)pyrimidin-4-one, or the enzyme superoxide dismutase.

EXAMPLE 1

Preparation of 1-(6-oxoheptyl)-3-methyl-7-propylxanthine 2.1 g of 3-methyl-7-propylxanthine, 0.7 g of 1-chloroheptan-6-one and 1.4 g of potassium carbonate are heated at 120° C. in 15 ml of dimethylformamide for 7.5 hours, while stirring. After the mixture has been concentrated under reduced pressure, the residue is poured into 100 ml of $H_2O$, the mixture is extracted three times with 100 ml of $CHCl_3$ each time, and the combined chloroform extracts are treated with 1 N sodium hydroxide solution and water in succession and dried over sodium sulfate. The concentration residue is chromatographed in a column using silica gel 60 and chloroform/ethanol (9:1) as the mobile phase. After recrystallization from petroleum ether/diisopropyl ether (3:1), 2.45 g (=76.6% yield) of 1-(6-oxoheptyl)-3-methyl-7-propylxanthine of melting point 69–70° C. are obtained.
$C_{16}H_{24}N_4O_3=320.40$ calculated: C 59.98% H 7.55% N 17.49%; found: C 59.81% H 7.53% N 17.65%.

The following compounds are prepared analogously to Example 1.

EXAMPLE 2

3-Ethyl-1-(5-oxohexyl)-7-propylxanthine (melting point 81–82° C.) is prepared from 3-ethyl-7-propylxanthine and 1-chlorohexan-5-one.

EXAMPLE 3

The ethylene ketal of 3-methyl-1-(4-oxopentyl)-7-propylxanthine is first obtained from 3-methyl-7-propylxanthine and 1-chloropentan-4-one ethylene ketal. This product is converted into 3-methyl-1-(4-oxopentyl)-7-propylxanthine (melting point 67–68° C.) by hydrolysis (1 hour/70° C.) in methanol/water (volume ratio 8:2) in the presence of 33% strength sulfuric acid.

EXAMPLE 4

1,3-Diethyl-7-(5-oxohexyl)xanthine (melting point 68–69° C.) is prepared from 1,3-diethylxanthine and 1-chloro-hexan-5-one.

EXAMPLE 5

1-(4-Oxo-3-methylpentyl)-3-methyl-7-propylxanthine
a) 1-Chloro-3-methylpentan-4-one
To a solution of 128.1 g (1 mol) of α-acetyl-γ-butyrolactone in 500 ml of absolute ethanol, 23.0 g (0.1 mol) of sodium are added in portions, while stirring. When the sodium has dissolved completely, 126.1 g (1 mol) of dimethyl sulfate are added dropwise, the reaction mixture heating up to the reflux temperature within 30 minutes. After the mixture has been heated at the reflux temperature for 1 hour and concentrated in vacuo, the oily residue is subjected to fractional distillation over a column. 106 g of α-acetyl-α-methyl-γ-butyrolactone are obtained (boiling points$_{14}$=119–122° C.), and are subjected directly to acid hydrolysis. For this, the above lactone is added dropwise to a boiling mixture of 200 ml of concentrated hydrochloric acid and 250 ml of water, and the reaction product is distilled over into a cooled receiver, $CO_2$ being evolved. Extraction with ether, drying over sodium sulfate and distillation of the organic residue over a column gives 92 g of 1-chloro-3-methylpentan-4-one of boiling point$_{16}$= 69–70° C.

b) 1-(4-Oxo-3-methylpentyl)-3-methyl-7-propylxanthine 25.0 g (0.12 mol) of 3-methyl-7-propylxanthine are stirred together with 16.2 g (0.12 mol) of 1-chloro-3-methylpentan-4-one (Example 5a) and 16.6 g (0.12 mol) of potassium carbonate in 300 ml of dimethylformamide at 140° C. for 8 hours. The solution is then evaporated under reduced pressure and the residue is rendered alkaline with dilute sodium hydroxide solution and extracted several times with chloroform. The combined chloroform extracts are washed neutral with a little water and dried over sodium sulfate, and the solvent is distilled off in vacuo, solid crude product being obtained, which is recrystallized from diisopropyl ether. Yield: 25.9 g (70% of theory) Melting point: 63–64° C.

$C_{15}H_{22}N_4O_3$ (molecular weight=306.4)

Analysis: calculated: C 58.81% H 7.24% N 18.29%; found: C 59.02% H 7.28% N 18.22%.

EXAMPLE 6

1-(4,4-Ethylenedioxy-3-methylpentyl)-3-methyl-7-propylxanthine a) Preparation of the 1,3-dioxolane of 1-chloro-3-methylpentan-4-one For this, 40.4 g (0.3 mol) of 1-chloro-3-methylpentan-4-one, 18.6 g (0.3 mol) of ethylene glycol and 0.5 g of p-toluenesulfonic acid are dissolved in 300 ml of toluene and the solution is heated under reflux using a water separator. Dilute sodium hydroxide solution is added to the organic phase which has separated out, and the mixture is extracted by shaking with ether. Drying of the organic phase over sodium sulfate and fractional distillation of the oily residue gives 37.6 g of the dioxolane (70% of theory) of boiling point$_{26}$= 47–50° C.

b) 1-(4,4-Ethylenedioxy-3-methylpentyl)-3-methyl-7-propylxanthine

Analogously to Example 5, 12.5 g (0.06 mol) of 3-methyl-7-propylxanthine are reacted with 12.0 g (0.067 mol) of the dioxolane (Example 6a) in the presence of 9.3 g (0.067 mol) of potassium carbonate in 150 ml of dimethylformamide. Yield: 18.2 g (86% of theory)

$C_{18}H_{28}N_4O_4$ (molecular weight=350.4) Melting point: 35–37° C.

Analysis: calculated: C 58.27% H 7.48% N 15.99%; found: C 58.35% H 7.70% N 15.82%.

The following compounds are prepared analogously to Example 5.

EXAMPLE 7

1-(4-Oxo-3-methylpentyl)-3-methyl-7-allylxanthine (melting point 73–74° C.) is prepared from 3-methyl-7-allylxanthine and 1-chloro-3-methylpentan-4-one.

EXAMPLE 8

1-(4-Oxo-3-methylpentyl)-3-ethyl-7-(2-methoxyethyl)-xanthine (melting point 83–84° C.) is prepared from 3-ethyl-7-(2-methoxyethyl)xanthine and 1-chloro-3-methylpentan-4-one.

EXAMPLE 9

1-(4-Hydroxy-3-methylpentyl)-3-methyl-7-propylxanthine

To a suspension of 9 g (0.029 mol) of 1-(4-oxo-3-methylpentyl)-3-methyl-7-propylxanthine (Example 5b) in 100 ml of methanol, 1.1 g (0.028 mol) of sodium borohydride are added, while stirring. After the mixture has been stirred for 2 hours, it is evaporated under reduced pressure, the residue is taken up in chloroform and the mixture is washed with dilute sodium hydroxide solution and water in succession, dried over sodium sulfate and concentrated to dryness. The yield of the highly viscous end product is 7.5 g (84% of theory).

$C_{15}H_{24}N_4O_3$ (molecular weight=308.4)

Analysis: calculated: C 58.42% H 7.84% N 18.17%; found: C 58.50% H 7.86% N 17.97%.

EXAMPLE 10

1-Ethoxymethyl-3-methyl-7-dimethylaminocarbonylmethylxanthine a) 3-Methyl-7-dimethylaminocarbonylmethylxanthine To a solution of 2 g (0.05 mol) of sodium hydroxide in 40 ml of water, 8.3 g (0.05 mol) of 3-methylxanthine and then 6.45 g (0.053 mol) of 2-chlorodimethylacetamide are added at 70° C. and the mixture is stirred at this temperature for a further 7 hours. After cooling, the residue which has precipitated is filtered off with suction, washed with water and methanol and dissolved in 2 N NaOH. When the pH is adjusted to 10 with 2 N $H_2SO_4$, a precipitate breaks out and, after the mixture has been stirred for 2 hours, is filtered off with suction, washed with water and dried at 100° C. Yield: 8.0 g.(64% of theory). Melting point: 336° C.

$C_{10}H_{13}N_4O_3$ (molecular weight=251.2).

Analysis: calculated: C 47.81% H 5.22% N 27.88%; found: C 47.92% H 5.10% N 27.36%.

b) 1-Ethoxymethyl-3-methyl-7-dimethylaminocarbonylmethylxanthine

To prepare the sodium salt of Example 10a, 0.92 g (0.04 mol) of sodium is dissolved in 160 ml of absolute methanol and 10 g (0.04 mol) of the compound from Example 10a are added. After the mixture has been heated to the reflux temperature for 15 minutes and after addition of 5.3 g (0.056 mol) of ethoxymethyl chloride in 150 ml of acetonitrile, heating is continued for a further 8 hours. Cooling and concentration of the solution gives a solid residue, which is dissolved in methylene chloride, dilute NaOH is then added and the mixture is then washed with water. Concentration of the phase which has been dried over sodium sulfate and recrystallization of the residue from ethanol leads to 1-ethoxymethyl-3-methyl-7-dimethylaminocarbonylmethylxanthine. Yield: 7.1 g (57% of theory) Melting point: 183–184° C.

$C_{13}H_{19}N_5O_4$ (molecular weight=309.3)

Analysis: calculated: C 58.48% H 6.19% N 22.64%; found: C 58.19% H 6.25% N 22.68%.

EXAMPLE 11

1,7-bis(Piperazinocarbonylmethyl)-3-methylxanthine a) Benzyl 1-piperazine-carboxylate 250 ml of water and 500 ml of methanol are added to 194 g (1 M) of piperazine hexahydrate, while stirring, and the pH is adjusted to 3 with about 163 ml of concentrated hydrochloric acid. The mixture is then cooled to 25° C. and 100 g (0.59 M) of benzyl chloroformate are added dropwise, while stirring, during which the pH is kept between 3 and 4.5 with sodium hydroxide solution (4 M; about 230 ml). About 700 ml are then stripped off on a rotary evaporator and the residue is washed with water, rendered acid with about 1.5 ml of concentrated HCl and extracted twice with 200 ml of toluene each time. The aqueous phase is cooled and brought to pH 12 with about 115 ml of 12.5 N NaOH. The oil which separates out is extracted several times with toluene, and the extract is dried over $K_2CO_3$ and concentrated under reduced pressure. Yield: 74 g Analysis: calculated: C 65.43% H 7.32%; found: C 65.32% H 7.65%.

$C_{12}H_{16}N_2O_2$ (molecular weight=220.2).

b) 4-Chloroacetyl-1-benzyloxycarbonyl-piperazine 110 g (0.5 M) of benzyl 1-piperazinecarboxylate are prepared, while stirring, as under a), 150 ml of methylene chloride are added at about –60° C., and 18.3 ml (0.23 M) of chloroacetyl chloride in 50 ml of methylene chloride are added dropwise in the course of 90 minutes, while stirring. The mixture is then warmed slowly to 25° C. and further stirred for 2 hours. The solution is washed with dilute hydrochloric acid, dilute sodium hydroxide solution and water in succession, dried over $Na_2SO_4$ and concentrated to dryness. The yield of highly viscous end product is 63 g.

Analysis: calculated: C 56.66% H 5.77% Cl 11.95% N 9.44%; found: C 56.53% H 5.8% Cl 11.47% N 9.45%.

$C_{14}H_{17}N_2O_3Cl$ (molecular weight=296.7).

c) 3-Methyl-1,7-bis(4-benzyloxycarbonyl-1-piperazinylcarboxymethyl)xanthine 5.4 g (0.0326 M) of 3-methylxanthine are stirred together with 21 g (0.0708 M) of the compound obtained according to b) in the presence of 10.7 g (0.0775 M) of $K_2CO_3$ in 100 ml of dimethylformamide (DMF) at 120–130° C. for 7 hours, and then filtered and washed with dimethylformamide. The filtrate is concentrated under reduced pressure to give 25 g of a highly viscous crude product.

d) 1,7-bis(Piperazinocarbonylmethyl)-3-methylxanthine 20 g of the crude product obtained in c) are gassed with $H_2$ in the presence of 2 g of palladium-on-charcoal in 200 ml of glacial acetic acid at about 75° C. for 8 hours, while stirring. The filtrate is concentrated and, after drying in a desiccator, the residue is dissolved in 150 ml of ethanol at 70° C. After treatment with active charcoal and addition of ethanolic HCl, the product precipitates in the form of the dihydrochloride. Yield: 11 g (80% of theory) Melting point: 338° C.

$C_{18}H_{26}N_8O_4$ (molecular weight=418.46).

The following Table 1 gives an overview of the compounds prepared.

TABLE 1

Compounds according to formula I

| Example | $R^1$ | $R^2$ | $R^3$ | Melting point ° C. |
|---|---|---|---|---|
| 1 | $CH_3-\underset{\underset{O}{\|\|}}{C}-(CH_2)_5-$ | $CH_3-$ | $C_3H_7-$ | 69–70 |
| 2 | $CH_3-\underset{\underset{O}{\|\|}}{C}-(CH_2)_4-$ | $C_2H_5-$ | $C_3H_7-$ | 81–82 |
| 3 | $CH_3-\underset{\underset{O}{\|\|}}{C}-(CH_2)_3-$ | $CH_3-$ | $C_3H_7-$ | 67–68 |
| 4 | $C_2H_5-$ | $C_2H_5-$ | $CH_3-\underset{\underset{O}{\|\|}}{C}-(CH_2)_4-$ | 68–69 |
| 5 | $CH_3-\underset{\underset{O}{\|\|}}{C}-\underset{\underset{CH_3}{\|}}{CH}-(CH_2)_2-$ | $CH_3-$ | $C_3H_7-$ | 63–64 |
| 6 | $\underset{O}{\overset{CH_3}{\diagdown}}\underset{\underset{O}{\diagup}}{\overset{\diagup}{C}}-\underset{\underset{CH_3}{\|}}{CH}-(CH_2)_2-$ | $CH_3-$ | $C_3H_7-$ | 35–37 |
| 7 | $CH_3-\underset{\underset{O}{\|\|}}{C}-\underset{\underset{CH_3}{\|}}{CH}-(CH_2)_2-$ | $CH_3-$ | $CH_2=CH-CH_2-$ | 73–74 |

TABLE 1-continued

Compounds according to formula I

| Example | R$^1$ | R$^2$ | R$^3$ | Melting point ° C. |
|---|---|---|---|---|
| 8 | CH$_3$—C(CH$_3$)(=O)—CH(CH$_3$)—(CH$_2$)$_2$— | C$_2$H$_5$— | CH$_3$—O—(CH$_2$)$_2$— | 83–84 |
| 9 | CH$_3$—CH(CH$_3$)—CH(OH)—(CH$_2$)$_2$— | CH$_3$— | C$_3$H$_7$— | Öl |
| 10 | CH$_3$—CH$_2$—O—CH$_2$— | CH$_3$— | (CH$_3$)$_2$N—C(=O)—CH$_2$— | 183—184 |
| 11 | HN(piperazine)N—C(=O)—CH$_2$— | CH$_3$— | HN(piperazine)N—C(=O)—CH$_2$— | 338 (2HCl) |

EXAMPLE 12
Pharmacological tests
Action on the partial pressure of oxygen in brain tissue In the model used here, the ability of a preparation to increase the partial pressure of oxygen in the cerebral cortex under physiological and/or pathological conditions, which can be interpreted as an indication of an improved metabolism in the brain, is measured.

Test animal: rat
Strain: genetically hypertensive rats (Mollegaard/Stroke Prone, Denmark)
Weight: 280–300 g
Sex: male
Administration: continuous infusion for 10 minutes 0.1 ml/minute 0.1–1 mg/kg
Procedure:

The test animal is anesthetized with 60 mg/kg i.p. of Na pentobarbital (Sigma).

Preparation:

The arteria femoralis is catheterized for measurement of the blood gases and blood pressure and the vena femoralis is catheterized for infusion of the test substance.

The trachea is then intubated and the head of the animal is fixed in a stereotactic frame. The cranial bone is exposed and a circular opening of about 3 mm is made by trepanning; the dura mater remains intact. The multiwire surface electrode is enriched with 2% or 12% of oxygen before the start of the experiment (calibration apparatus for O$_2$ and C$_{O2}$ gas partial measurements, Rhema).

The electrode is gently placed on the trepanned cerebral surface by means of a micromanipulator (Brinkmann, Mannheim) and surrounded with 0.9% NaCl. After a stable physiological starting situation has been reached, the course of the O$_2$ and CO$_2$ values with respect to time is recorded.

The test substance (0.1 ml/minute) is infused in a normal dosage of 1 mg/kg/minute for a period of 10 minutes. The number of test animals for one test substance is in each case 5 to 6.

Table 2 shows the results in percent in comparison with a control, where physiological saline solution is infused instead of the test substance.

TABLE 2

| Compound according to Example | Change in the partial pressure of oxygen in comparison with the control (%) |
|---|---|
| Control | 0 |
| 1 | +34 |
| 2 | +23 |
| 3 | +13 |
| 4 | +14 |
| 5 | +40 |
| 6 | +33 |
| 7 | +15 |
| 8 | +15 |
| 9 | +9 |
| 10 | +10 |
| 11 | +12 |

What is claimed is:

1. A compound of the formula 1-(4,4-ethylenedioxy-3-methylpentyl)-3-methyl-7-propylxanthine.

2. A compound of the formula 1-(4-oxo-3-methylpentyl)-3-methyl-7-allylxanthine.

3. A compound of the formula 1-(4-oxo-3-methylpentyl)-3-ethyl-7-(2-methoxyethyl)-xanthine.

4. A compound of the formula 1-ethoxymethyl-3-methyl-7-dimethylamino-carbonylmethyl-xanthine.

5. A compound of the formula 1,7-bis (piperazinocarbonylmethyl)-3-methylxanthine.

* * * * *